US00PP27768P3

(12) United States Plant Patent
Danziger

(10) Patent No.: US PP27,768 P3
(45) Date of Patent: Mar. 7, 2017

(54) LAVENDER PLANT NAMED 'DLAVENLPOP'

(50) Latin Name: *Lavandula stoechas*
Varietal Denomination: DLAVENLPOP

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 61 days.

(21) Appl. No.: 14/545,174

(22) Filed: Apr. 1, 2015

(65) Prior Publication Data

US 2016/0295791 P1 Oct. 6, 2016

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Anne Grunberg
(74) *Attorney, Agent, or Firm* — Cassandra Bright

(57) ABSTRACT

A new and distinct Lavender cultivar named 'DLAVENLPOP' is disclosed, characterized by pink flowers and terminal bracts, uniform inflorescence and very compact plant form. The new variety is a *Lavandula*, normally produced as an outdoor garden or container plant.

2 Drawing Sheets

Latin name of the genus and species: *Lavandula stoechas*.
Variety denomination: 'DLAVENLPOP'.

BACKGROUND OF THE INVENTION

The new *Lavandula* cultivar is a product of a planned breeding program conducted by the inventor, Gavriel Danziger, in Moshav Mishmar Hashiva, Israel. The objective of the breeding program was to produce new Lavender varieties for ornamental commercial applications. The open pollination resulting in this new variety was made during March of 2010.

The seed parent is the, unpatented, proprietary variety referred to as Lavender 'LA-10-2000'. The pollen parent is unknown as it was an open pollination breeding program. The new variety was discovered in March of 2011 by the inventor in a group of seedlings resulting from the 2010 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in March of 2011 and has shown that the unique features of this cultivar are stable and reproduced true to type in multiple successive generations.

SUMMARY OF THE INVENTION

The cultivar 'DLAVENLPOP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLAVENLPOP' These characteristics in combination distinguish 'DLAVENLPOP' as a new and distinct Lavender cultivar:

1. Very compact plant.
2. Uniform inflorescence.
3. Pink flowers and terminal bracts.

Plants of the new cultivar 'DLAVENLPOP' are similar to plants of the seed parent, Lavender 'LA-10-2000' in most horticultural characteristics, however, plants of the new cultivar 'DLAVENLPOP' differ in the following;

1. Flowers earlier.
2. More flowers forming on one spike.
3. Lighter flower color.

COMMERCIAL COMPARISON

Plants of the new cultivar 'DLAVENLPOP' are comparable to the unpatented commercial variety Lavender 'DLAVENGPUR'. The two Lavender varieties are similar in most horticultural characteristics; however, the new variety 'DLAVENLPOP' differs in the following:

1. Smaller terminal bracts.
2. More flower spikes.

Plants of the new cultivar 'DLAVENLPOP' can also be comparable to the unpatented commercial variety Lavender 'DLAVEN31'. The two Lavender varieties are similar in most horticultural characteristics; however, the new variety 'DLAVENLPOP' differs in the following:

1. The new variety produces flowers the same color as the terminal bracts whereas the comparator produces flowers differing in color from the terminal bracts.
2. Plant habit of the new variety is more spreading and plant habit is more full than the comparator.
3. The new variety has a more uniformed flowering habit.

BRIEF DESCRIPTION OF THE PHOTOGRAPHS

Figure 1:
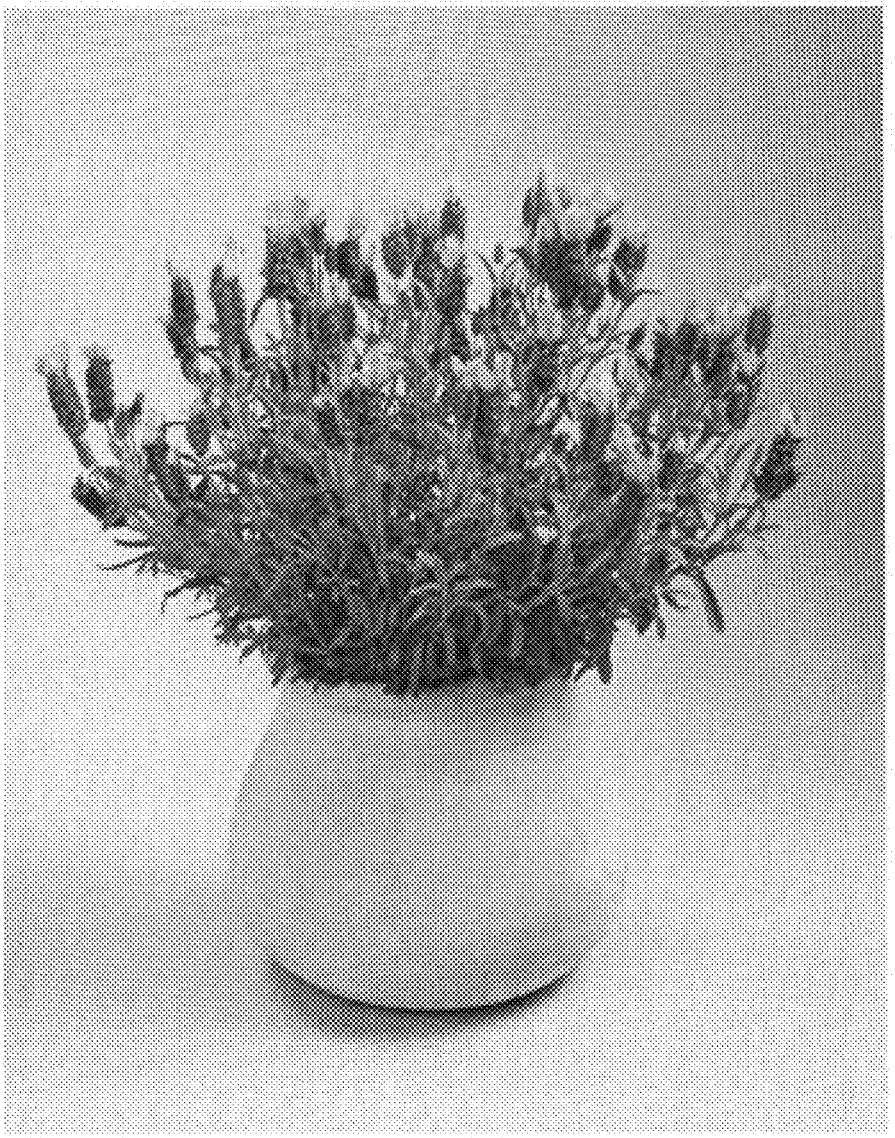

The accompanying photograph in FIG. 1 illustrates in full color a typical plant of 'DLAVENLPOP' grown outdoors, in a 16 cm pot. Age of the plant photographed is approximately 24 weeks from a rooted cutting.

Figure 2:
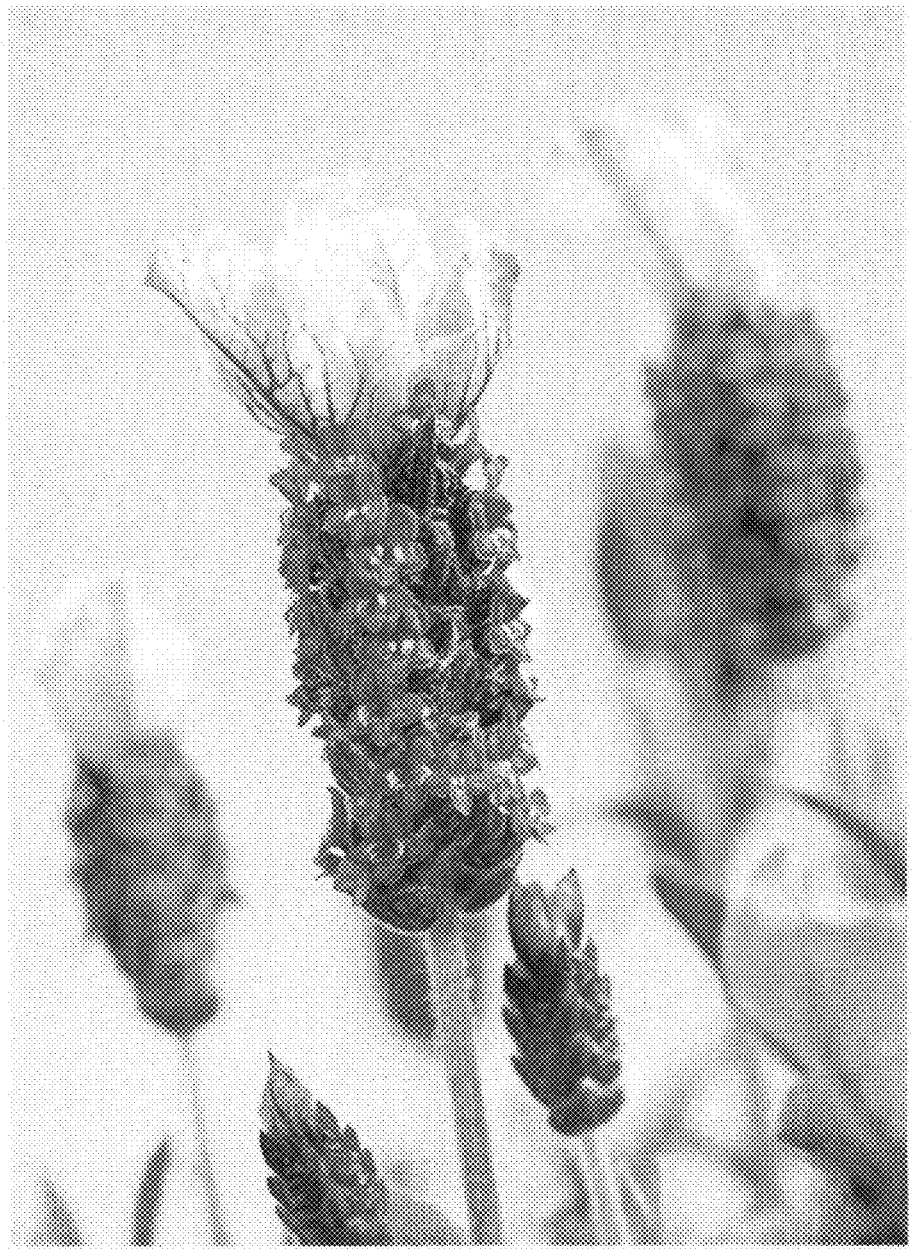

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DLAVENLPOP' plants grown in the Autumn, in a greenhouse, in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types.

Botanical classification: Lavender 'DLAVENLPOP'.

PROPAGATION

Time to initiate roots: About 4 weeks at temperatures of 64-75° F. (18-24° C.), rooting hormone can be used to promote early, uniform rooting.

Time to produce a rooted cutting: About 21-28 days at temperatures of 64-75° F. (18-24° C.).

PLANT

Age of plant described: Approximately 24 weeks from a rooted cutting.

Plant spread: Approximately 30-35 cm.

Plant height: 20 cm.

Growth rate: Moderate.

Length of primary lateral branches: Approximately 18 cm.

Diameter of lateral branches: Approximately 0.2 cm.

Quantity of lateral branches: About 50.

Branches:

- *Color*.—Near Yellow-green group 144D RHS.
- *Texture/pubescence*.—Pulverulent.

Internode length: Approximately 1.5 cm.

FOLIAGE

Leaf:

- *Arrangement*.—Opposite.
- *Quantity*.—Approximately 80 per main branch.
- *Average length*.—Approximately 2 cm.
- *Average width*.—Approximately 0.5 cm.
- *Shape of blade*.—Oblong.
- *Apex*.—Acute.
- *Base*.—Cuneate.
- *Attachment*.—Sessile.
- *Margin*.—Entire.
- *Texture of top surface*.—Velvety.
- *Pubescence*.—A few.
- *Color*.—Young foliage upper side: Near Green group 138A RHS. Young foliage under side: Near Green group 138B RHS. Mature foliage upper side: Near Green group 138A RHS. Mature foliage under side: Near Green group 138B RHS.
- *Venation*.—Type: Pinnate. Venation color upper side: Near Green group 138B RHS. Venation color under side: Near Green group 138B RHS.
- *Petiole*.—Not present.

FLOWER

Bloom period: Flowering begins early Spring, with the heaviest flush occurring until approximately April and May. Flowering continues in lesser flushes until Fall. Inflorescence lastingness on the plant varies from four to six weeks, depending significantly on environmental conditions.

Inflorescence:

- *Form*.—Small single flower in verticillasters arranged in spikes. Flowers have small bracts, and large showy terminal bracts.
- *Quantity of rows of flowers per verticillaster*.—7 to 9.
- *Florets*.—Corolla tube is 2-lipped.
- *Size individual flowers*.—Length: Approximately 0.5 cm. Diameter: Approximately 0.2 cm.
- *Inflorescence size, excluding terminal bracts*.—Length: Approximately 4 cm. Width: Approximately 1 cm.
- *Coloration of individual flowers and entire spikes, excluding terminal bracts*.—Immature: Near Purple group 75A RHS. Mature: Near Purple group 75A RHS. Fading: Near Purple group 72B RHS.

Terminal bracts:

- *Quantity*.—4.
- *Length*.—Approximately 1.5 cm.
- *Width*.—Approximately 1 cm.
- *Aspect*.—Undulating.
- *Duration on plant*.—Approximately 8-10 weeks, with good color. Persistent.
- *Color*.—Upper side of immature bract: Near Purple group 75B RHS. Under side of immature bract: Near Purple group 75A RHS. Upper side of mature bract: Near Purple group 77C RHS. Under side of mature bract: Near Red Purple group N74C RHS.

Fragrance: Leaves and flowers emit a delicate lavender fragrance.

Peduncle:

- *Peduncle length*.—Approximately 3.5 cm.
- *Peduncle diameter*.—Approximately 0.2 cm.
- *Aspect*.—Upright.
- *Color*.—Near Yellow-green group 144A RHS.

REPRODUCTIVE ORGANS

Stamens:

- *Number*.—4.
- *Filament length*.—Approximately less than 0.5 cm.

Anthers:

- *Shape*.—Reniform.
- *Length*.—Approximately less than 0.5 cm.
- *Color*.—Near Greyed orange group 166D RHS.
- *Pollen*.—Color: Near Greyed green group 196D RHS. Quantity: Few.

Pistil:

- *Number*.—1.
- *Length*.—Approximately 0.4 cm.
- *Style*.—Length: Approximately 0.35 cm. Color: Near White group NN155 RHS.
- *Stigma*.—Shape: Club-shaped. Color: Near White group NN155 RHS. Ovary color: Near Yellow-green group 144B RHS.

OTHER CHARACTERISTICS

Seeds and fruits: Seed and fruit production has not been observed.

Disease/pest resistance: Neither resistance nor susceptibility observed. *Lavandula* is not affected by many diseases and pests. However, *Botrytis* and some root rot pathogens can be diseases problems, especially in overly wet conditions. Various species of White Fly may infect *Lavandula*.

Temperature tolerance: High temperature and low temperature tolerance are not known.

Optimum temperature: Day: 64-75° F. (18-24° C.). Night: 52-62° F. (11-17° C.).

What is claimed is:

1. A new and distinct cultivar of *Lavandula* plant named 'DLAVENLPOP' as herein illustrated and described.

* * * * *